United States Patent [19]
Caillouette

[11] Patent Number: 5,651,372
[45] Date of Patent: Jul. 29, 1997

[54] BIOPSY SYRINGE

[76] Inventor: James C. Caillouette, 685 Oak Knoll Cir., Pasadena, Calif. 91105

[21] Appl. No.: 496,039

[22] Filed: Jun. 28, 1995

[51] Int. Cl.$^6$ ................................. A61B 10/00
[52] U.S. Cl. .................. 128/753; 128/765; 604/187; 604/210; 604/220
[58] Field of Search ............... 128/749, 752, 128/753, 754, 758, 763, 765, 766; 604/187, 208, 210, 218, 220

[56] References Cited

U.S. PATENT DOCUMENTS

| | | |
|---|---|---|
| 1,520,795 | 4/1924 | Barr . |
| 3,727,602 | 4/1973 | Hyden et al. ............... 128/2 B |
| 3,938,505 | 2/1976 | Jamshidi ..................... 128/2 B |
| 4,405,308 | 9/1983 | Jessup ......................... 604/200 |
| 4,549,554 | 10/1985 | Markham ................... 128/753 |
| 4,552,155 | 11/1985 | Etherington et al. ...... 128/766 |
| 4,619,272 | 10/1986 | Zambelli ..................... 128/753 |
| 5,246,011 | 9/1993 | Caillouette ................. 128/753 |

*Primary Examiner*—Sam Rimell
*Assistant Examiner*—Robert V. Racunas
*Attorney, Agent, or Firm*—William W. Haefliger

[57] ABSTRACT

A control syringe is provided for fine needle aspiration of biopsy tissue. An aperture through the barrel of the syringe is located at a rearward position of the barrel. A low pressure created in the barrel by withdrawing the plunger is broken by withdrawing the plunger past the aperture. Thereafter, the plunger may be pushed forward of the aperture so that collected tissue may be discharged by moving the plunger forward. A detent attached to the plunger holds the plunger in its rearward position until released. The detent comprises a plastic member with an outwardly biased shoulder for engaging the rearward end of the barrel. Such a detent is released by pressing it towards the plunger.

9 Claims, 2 Drawing Sheets

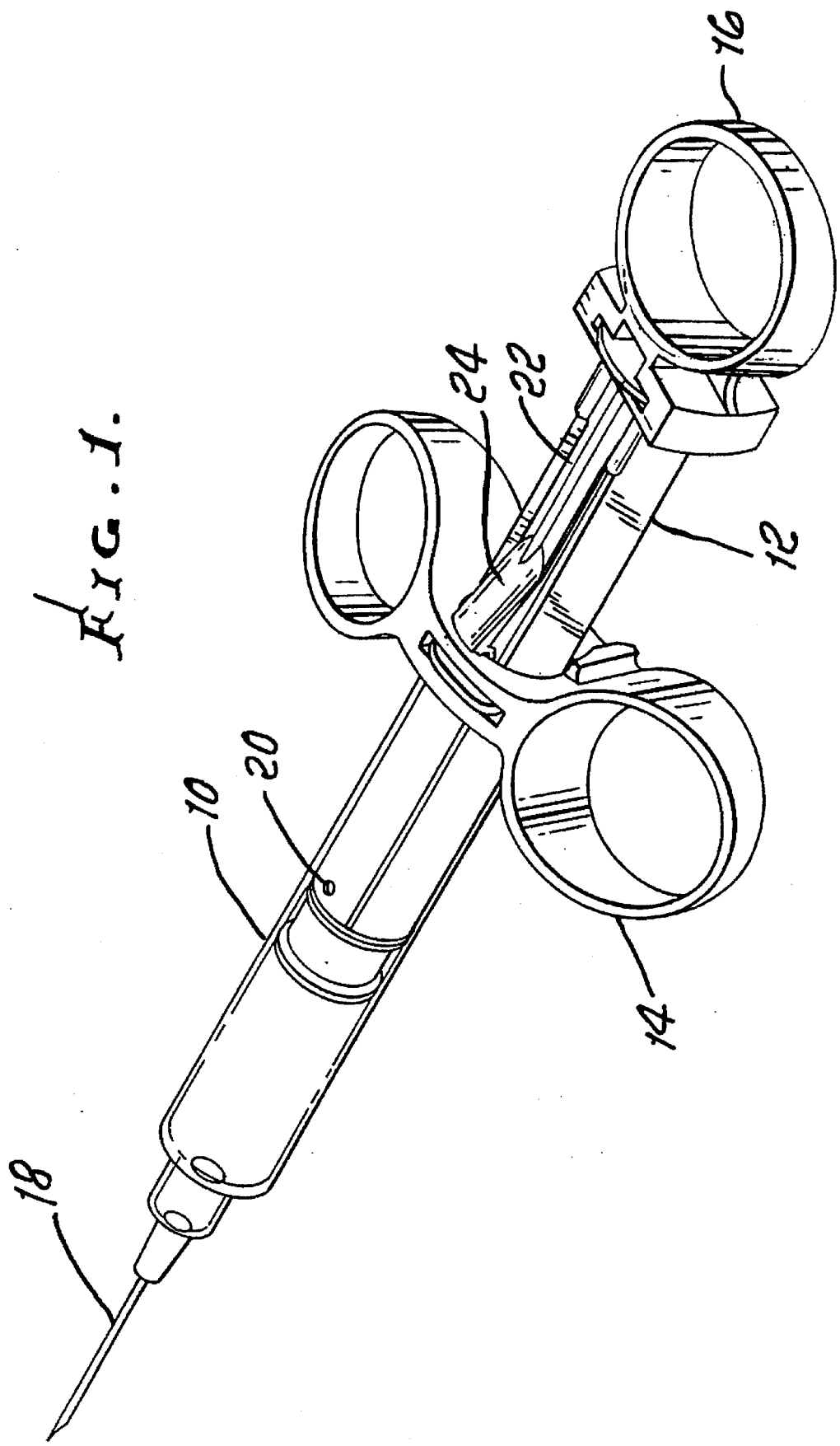

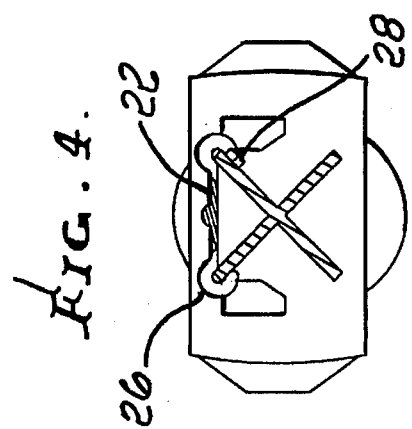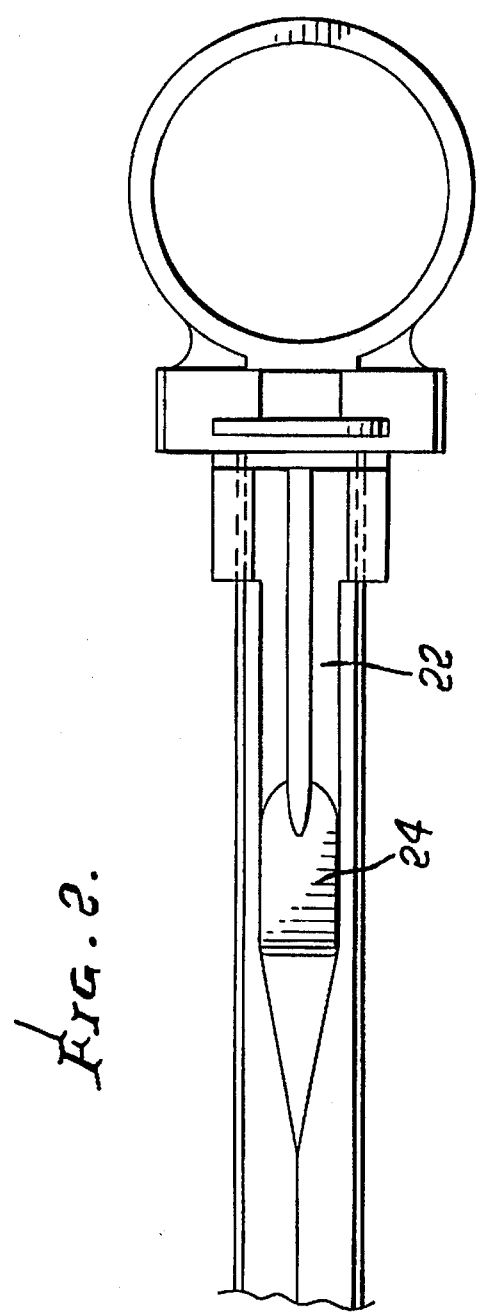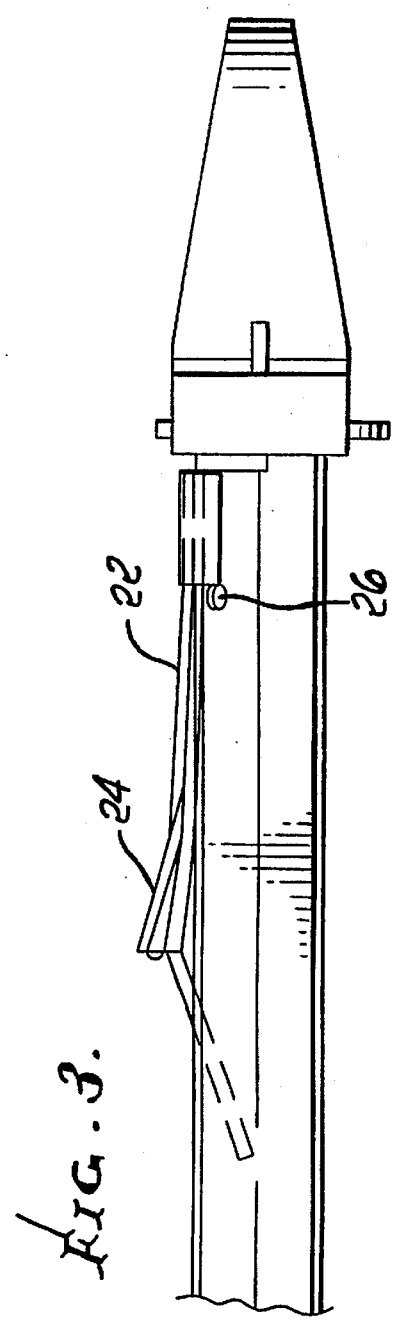

BIOPSY SYRINGE

BACKGROUND OF THE INVENTION

This invention relates to a syringe for drawing and releasing a vacuum so that the syringe may be used for obtaining a sample of tissue for a biopsy.

A technique which is useful for obtaining tissue samples for a biopsy is known as fine needle aspiration. When a physician suspects tissue observed by x-ray, ultrasound, or palpation may be cancerous, it is usually desirable to obtain a sample of the tissue for microscopic examination. The fine needle aspiration technique is used, for example, for sampling what appear to be lung lesions, lumps in the breast, dense prostrate tissue, or other anomalous portions of body organs.

A hollow needle or cannula is inserted, typically through the skin, so that the tip of the needle is in the suspect tissue. The plunger of the syringe is then withdrawn to pull a small amount of tissue into the hollow needle. The needle is withdrawn and the tissue sample discharged onto a slide for examination. Such aspiration of tissue into the needle may be performed in several locations in suspected tissue with a single insertion of the needle into the body.

In a typical examination using fine needle aspiration, the physician may palpate a breast to isolate and grasp a lump with one hand, and with the other hand guide the needle of an aspiration syringe into the lump. A "control" syringe may be used with finger grips on the barrel and plunger of the syringe so as to draw a vacuum in the barrel once the needle is in the lump.

At that point it becomes desirable to release the vacuum in the syringe. Failure to do so when the needle is withdrawn from the body may result in the tissue being drawn through the needle into the barrel of the syringe, where it may be lost and unavailable for biopsy. The vacuum in the barrel should not be released by simply pressing the plunger forward again since this could prematurely discharge the tissue from the needle, even before it is withdrawn from the body.

It is also desirable to introduce air into the syringe so that when the plunger is returned toward the end of the syringe, pressure in the barrel discharges tissue onto a slide for microscopic examination. It is also important for some fine needle aspiration procedures that the physician be able to operate the device entirely with one hand, at least until a sample is obtained, so that the other hand may be used to know or hold the position of the lump. Obtaining a sample of breast tissue is a good example. Breast cancer is of increasing concern for women. Improved methods for diagnosis are essential.

SUMMARY OF THE INVENTION

There is, therefore, provided in practice of this invention according to a presently preferred embodiment, a fine needle aspiration syringe comprising a barrel and a plunger sealed in the barrel for drawing a vacuum in the barrel when the plunger is withdrawn toward a rearward position. An aperture through a side of the barrel permits air flow into the barrel for breaking a vacuum, the aperture being placed at such a position on the barrel that withdrawal of the plunger to a position forward of the aperature will result in a lowered pressure in the forward end of the syringe sufficient to draw a tissue sample into the needle.

Preferably the syringe also includes a detent mounted on the plunger and outwardly biased for engaging the rearward end of the barrel. This permits easy withdrawal of the plunger for creating a vacuum and inhibits return of the plunger so that the vacuum can be temporarily maintainted.

Means are also provided for releasing the detent for returning the plunger. A stylet may be fastened to the forward end of the plunger for plugging a hollow needle on the syringe when the plunger is in its forward position for excluding tissue from the hollow needle during its insertion into tissue.

BRIEF DESCRIPTION OF THE DRAWINGS

These and other features and advantages of the present invention will be appreciated as the same becomes better understood by reference to the following detailed description when considered in connection with the accompanying drawings wherein:

FIG. 1 illustrates isometrically a fine needle aspiration syringe constructed according to principles of this invention;

FIG. 2 illustrates a top view of a detent attached to the syringe plunger for permitting withdrawal and inhibiting return of the plunger;

FIG. 3 illustrates a side view of a detent and a positioning knob; and

FIG. 4 illustrates in cross-section a detent with sleeves attached to the ribs of a syringe plunger and a positioning knob on a rib and forward of one of the detent sleeves.

DETAILED DESCRIPTION

An aspiration syringe comprises a cylindrical barrel 10 with a movable plunger 12, one end of which is sealed in the barrel, typically by an O-ring, integrally fitted end cap, or the like so that as the plunger slides along the barrel, no fluid can pass the seal. Typically a so-called control syringe is used which has finger grips 14 secured to the barrel and a thumb ring 16 on the end of the plunger. The person operating the syringe places the forefinger and middle finger in the finger grips on the barrel, and the thumb in the ring on the plunger so that the operator has good control of the syringe position and the plunger can be moved in the barrel in either direction with one hand.

A hollow needle or cannula 18 is mounted on the forward end of the barrel in a conventional manner. If desired, a solid stylet having a diameter only slightly smaller than the internal diameter of the cannula is mounted on the forward end of the plunger. Thus, when the plunger is in its forward position, the stylet extends most of the way through the hollow needle and plugs it. The stylet is withdrawn from the needle when the plunger is withdrawn toward a rearward position in the barrel.

An aperture 20 is provided through the side wall of the barrel at a location relatively nearer the rearward end of the barrel and relatively further from the forward end of the barrel. When the syringe is used, the needle is inserted into the patient's body until the tip is in the tissue to be sampled. As the plunger is withdrawn toward a rearward position in the barrel, a partial vacuum is created in the forward portion of the syringe while the end of the plunger sealed in the barrel remains forward of the aperture. Withdrawing the plunger also withdraws the stylet from the needle. The partial vacuum in the forward end of the syringe draws tissue into the needle. If desired, the needle can be probed into different portions of the tissue to acquire samples from various locations.

When an adequate sample has been obtained, the plunger can be withdrawn to a position behind the aperture, thereby venting air into the barrel and releasing the vacuum. The needle can then be withdrawn from the tissue with a sample in the needle.

In this manner, the syringe can be operated with one hand during the entire procedure while the other hand is used for palpation of the tissue or for holding the mass in place.

To discharge the sample, the plunger is depressed into the barrel to a position forward of the aperture. Once the forward end of the plunger is pushed beyond the aperture, air will no longer vent out of the aperture, and the forward end of the syringe will experience increased pressure which will cause the sample to be ejected from the needle.

It is often desirable that the vacuum be maintained in the forward end of the syringe for a time. If the operator releases the plunger it could be pressed forward by external air pressure, thereby decreasing the vacuum and prematurely discharging the tissue sample. Means are therefore provided for inhibiting return of the plunger toward the forward position until desired.

One means for doing this comprises attaching a conventional detent 22 to the plunger. Most of the disposable plastic syringes in use today have a plunger with an X-shaped cross-section. The detent comprises a plastic member attached between a pair of the ribs and having an outwardly biased shoulder 24 for engaging the rearward end of the barrel.

The detent has sleeves 26 at its rearward end which attach to the ribs on the plunger as illustrated in FIG. 4. A positioning knob 28 is placed on a rib forward of one of the sleeves to prevent the detent from sliding below that position.

The detent can be positioned on the plunger that when the plunger is withdrawn to a position in the barrel sufficient to create an aspiration vacuum, i.e., a sufficiently low pressure in the barrel to draw tissue into the needle, the detent will spring outwardly and engage the rearward end of the barrel. Once engaged, the detent will prevent advance of the plunger toward the forward end of the barrel, thereby maintaining the aspiration vacuum. For example, a typical aspiration vacuum for a breast biopsy is created by a stroke of 6 to 8 milliliters on a 10 milliliter syringe. When the user desires to move the plunger forward, all that is needed is to press in the detent toward the axis of the syringe, thereby disengaging it from the rear end of the barrel.

Although limited embodiments of fine needle aspiration syringe have been described herein, many modifications and variations will be apparent to those skilled in the art. For example, depending on the size of the syringe, the aperture may be placed at a position nearer the forward end of the barrel and still permit the creation of an aspiration vacuum in the forward end of the syringe upon withdrawal of the plunger. Also, other detents for preventing advance of the plunger toward the forward end of the barrel may be used. It is therefore to be understood that within the scope of the appended claims, the invention may be practiced otherwise than as specifically described.

What is claimed is:

1. In syringe apparatus for retrieving body tissue samples, the combination comprising
   a) the syringe apparatus having a barrel, a needle carried by the barrel, and a plunger movable in the barrel,
   b) a detent slidably connected to the plunger, the detent having a barrel-engaging shoulder,
   c) the detent shoulder biased inwardly in a first forward position of the plunger in the barrel at which time the needle may be inserted into body tissue to be sampled,
   d) the detent shoulder biased outwardly in a second position of the plunger in the barrel to which the plunger is withdrawn to create suction in a barrel chamber forward of the plunger and communicated to the needle to effect drawing of a body tissue sample into the needle,
   e) the barrel having a side wall through opening, and the plunger having a position in the barrel to which it is withdrawn past said through opening to allow releasing of said suction in said forward chamber, thereby to prevent further drawing of body tissue into the needle,
   f) whereby the detent shoulder in said second position prevents forward movement of the plunger which would cause pressurization of air in said chamber in the barrel, as during transport of the syringe to a location where body tissue is to be expelled from the needle for retrieval.

2. Syringe apparatus as recited in claim 1 wherein the barrel comprises a pair of finger grips on opposite sides and the plunger comprises a finger grip on its rearward end for withdrawing the plunger with one hand.

3. Syringe apparatus as recited in claim 1 wherein the through opening is positioned on the barrel such that a portion of the barrel between the opening and a forward end of the barrel has a volume in the range from four to ten milliliters.

4. Syringe apparatus as recited in claim 1 further comprising:
   a hollow needle on an end of the syringe; and
   a stylet mounted on the plunger extending into the needle for plugging the needle when the plunger is forward in the barrel and clearing the needle when the plunger is withdrawn toward a rearward part of the barrel.

5. Syringe apparatus as recited in claim 1 wherein the plunger comprises four longitudinal ribs forming an X-shaped transverse cross section and the detent comprises an insert between a pair of the ribs.

6. Syringe apparatus as recited in claim 1 further comprising means for releasing the detent and permitting return of the plunger.

7. Syringe apparatus as recited in claim 1 further comprising a means for restricting movement of the detent lengthwise of the plunger.

8. Syringe apparatus as recited in claim 7 wherein the means for restricting movement of the plunger comprises a positioning knob placed on a plunger rib to which the detent is attached.

9. The method of retrieving body tissue samples, using a syringe having a needle, a barrel, and a plunger movable in the barrel, which includes the steps:
   a) providing a detent slidably connected to the plunger, providing a barrel-engaging shoulder on the detent, and biasing the detent shoulder inwardly in a first forward position of the plunger in the barrel,
   b) inserting the needle into body tissue to be sampled,
   c) withdrawing the plunger to a second position in the barrel to create suction in a chamber in the barrel forward of the plunger, and communicated to the needle to effect drawing of a body tissue sample into the needle, and allowing the detent shoulder to become biased outwardly,
   d) providing a side opening in the barrel and relieving said suction via said opening after the plunger has been withdrawn past said opening and to a predetermined position in the barrel, thereby to prevent further drawing of body tissue into the needle,
   e) whereby the detent shoulder in said second position of the plunger prevents forward movement of the plunger, which would cause pressurization of air in said chamber in the barrel, as during transport of the syringe to a locus where body tissue is expelled from the needle onto a test platform.

\* \* \* \* \*